(12) United States Patent
Ihori et al.

(10) Patent No.: US 9,006,632 B2
(45) Date of Patent: Apr. 14, 2015

(54) SOLID-STATE IMAGING DEVICE HAING A CONTROL SECTION CONTROLLING INITIALIZING OPERATION OF PIXEL UNITS BASED ON AN ABSOLUTE VALUE OF TRIGGER DATA OUTPUT

(75) Inventors: Atsushi Ihori, Hamamatsu (JP); Yukinobu Sugiyama, Hamamatsu (JP); Keisuke Nakao, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 160 days.

(21) Appl. No.: 13/639,349

(22) PCT Filed: Feb. 8, 2011

(86) PCT No.: PCT/JP2011/052654
§ 371 (c)(1),
(2), (4) Date: Oct. 25, 2012

(87) PCT Pub. No.: WO2011/129143
PCT Pub. Date: Oct. 20, 2011

(65) Prior Publication Data
US 2013/0037699 A1 Feb. 14, 2013

(30) Foreign Application Priority Data

Apr. 14, 2010 (JP) .............................. P2010-093099

(51) Int. Cl.
*H01L 27/00* (2006.01)
*H04N 5/32* (2006.01)
*H04N 5/351* (2011.01)
*H04N 5/353* (2011.01)
*H04N 5/3745* (2011.01)
*A61B 6/00* (2006.01)
*H01L 27/146* (2006.01)
*A61B 6/14* (2006.01)

(52) U.S. Cl.
CPC ........... *H04N 5/3745* (2013.01); *A61B 6/4208* (2013.01); *H01L 27/14609* (2013.01); *A61B 6/145* (2013.01); *A61B 6/54* (2013.01)

(52) U.S. Cl.
CPC ................. *H04N 5/32* (2013.01); *H04N 5/351* (2013.01); *H04N 5/3532* (2013.01);

(Continued)

(58) Field of Classification Search
USPC ................ 250/208.1, 214 R, 370.08, 370.09, 250/336.1; 378/19, 20; 348/292–313; 257/291, 292, 440
See application file for complete search history.

(56) References Cited

U.S. PATENT DOCUMENTS 6,069,935 A 5/2000 Schick et al.
6,307,915 B1 10/2001 Fröjdh (Continued)

FOREIGN PATENT DOCUMENTS

EP 1 677 514 7/2006
JP 09-131337 5/1997

(Continued)

OTHER PUBLICATIONS

U.S. Office Action dated Jul. 22, 2014 that issued in U.S. Appl. No. 13/640,386 including Double Patenting Rejections on pp. 2-3.
International Preliminary Report on Patentability (IPRP) dated Nov. 15, 2012 that issued in WO Patent Application No. PCT/JP2011/052653.
International Preliminary Report on Patentability (IPRP) dated Nov. 15, 2012 that issued in WO Patent Application No. PCT/JP2011/052654.

*Primary Examiner* — Que T Le
(74) *Attorney, Agent, or Firm* — Drinker Biddle & Reath LLP

(57) ABSTRACT

The solid-state imaging device 1 includes an imaging photo-detecting section 10, a trigger photodetecting section 20, a row selection section 30, a column selection section 40, a holding section 50, a pixel data output section 60, a trigger data output section 70, and a control section 80. The control section 80, when an absolute value of trigger data has changed into a state of being in excess of a first threshold, and then the state has continued for a predetermined time $\tau_1$ or more, judges it as a start of a light incidence, and starts a charge accumulating operation for each pixel unit, and when an absolute value of trigger data has changed into a state of being less than a second threshold, and then the state has continued for a predetermined time $\tau_2$ or more, judges it as an end of a light incidence, and causes a charge transferring operation and a data outputting operation to be performed for each pixel unit. Accordingly, a solid-state imaging device that can perform accurate imaging even for various applications and light incidence patterns is realized.

3 Claims, 16 Drawing Sheets

(56) References Cited

U.S. PATENT DOCUMENTS

| | | | | |
|---|---|---|---|---|
| 7,755,056 | B2 * | 7/2010 | Bell | ............ 250/370.09 |
| 2003/0083564 | A1 | 5/2003 | Ghelmansarai et al. | |
| 2010/0084564 | A1 | 4/2010 | Moody et al. | |
| 2013/0112851 | A1 | 5/2013 | Ihori et al. | |

FOREIGN PATENT DOCUMENTS

| JP | 11-155847 | 6/1999 |
|---|---|---|
| JP | 11-188033 | 7/1999 |
| JP | 2002-505002 | 2/2002 |
| JP | 2005-064550 | 3/2005 |
| JP | 2005-160929 | 6/2005 |
| JP | 2006-148901 | 6/2006 |
| JP | 2006-191236 | 7/2006 |
| JP | 2006-246961 | 9/2006 |
| JP | 2007-043324 | 2/2007 |
| JP | 2007-295189 | 11/2007 |
| JP | 2008-131485 | 6/2008 |

\* cited by examiner

SOLID-STATE IMAGING DEVICE HAING A CONTROL SECTION CONTROLLING INITIALIZING OPERATION OF PIXEL UNITS BASED ON AN ABSOLUTE VALUE OF TRIGGER DATA OUTPUT

TECHNICAL FIELD

The present invention relates to a solid-state imaging device having a photodetecting section where a plurality of photodiodes each of which generates charge of an amount according to an incident light amount are two-dimensionally arrayed, and more particularly, to a solid-state imaging device that can be suitably used for intraoral X-ray imaging.

BACKGROUND ART

A solid-state imaging device intended to be used for intraoral X-ray imaging has been disclosed in Patent Document 1. For such application, the incident period of X-rays to be imaged is considerably short, so that the solid-state imaging device must capture the timing of incidence of X-rays to image the X-rays. Therefore, the solid-state imaging device disclosed in Patent Document 1 includes not only an imaging photodetecting section where pixel units including photodiodes are two-dimensionally arrayed in order to take an X-ray image but also separately a trigger photodiode for detecting an incidence of X-rays. And, this solid-state imaging device detects an incidence of X-rays by monitoring an electrical signal output from the trigger photodiode and then obtains an X-ray image based on an electrical signal output from the imaging photodetecting section.

Moreover, solid-state imaging devices can be divided based on configuration into an APS (Active Pixel Sensor) type and a PPS (Passive Pixel Sensor) type. The solid-state imaging device disclosed in Patent Document 1 is of an APS type. A pixel unit in the case of an APS type includes a photodiode for generating charge of an amount according to an incident light amount, a floating diffusion region serving as a charge accumulating section for accumulating the charge, and an amplifying transistor having a gate electrode electrically connected with the floating diffusion region.

The APS type solid-state imaging device can, at the same timing in the plurality of pixel units of the photodetecting section, discharge a junction capacitance section of the photodiode and the floating diffusion region, generate charge in the photodiode, transfer the generated charge to the floating diffusion region, and accumulate the transferred charge in the floating diffusion region. Then, this solid-state imaging device can, in order row by row in the photodetecting section, output data according to an amount of charge accumulated in the floating diffusion region of each pixel unit from the amplifying transistor. This imaging operation is called a global shutter type.

In contrast thereto, in a rolling shutter type imaging operation, charge generation in the photodiode, charge accumulation, and data output are performed in order with a shift of the period row by row in the photodetecting section. In the rolling shutter type imaging operation, respective frames of image data obtained by imaging are data obtained at different times depending on the row.

In a global shutter type imaging operation, respective frames of image data obtained by imaging are data obtained at the same time regardless of the row. Therefore, when the incident period of light to be imaged is considerably short as in intraoral X-ray imaging, the global shutter type imaging operation is preferred.

CITATION LIST

Patent Literature

Patent Document 1: Japanese Translation of PCT International Application No. 2002-505002

SUMMARY OF INVENTION

Technical Problem

Meanwhile, the solid-state imaging device disclosed in Patent Document 1 intends to detect the start and end of an incidence of X-rays by monitoring an electrical signal output from the trigger photodiode and to image X-rays made incident on the imaging photodetecting section in a period during which X-rays are made incident. However, depending on the application and light incidence pattern, the start or end of a light incidence may be erroneously detected in some cases, and in those cases, the solid-state imaging device cannot perform accurate imaging.

The present invention has been made in order to solve the above-described problem, and an object thereof is to provide a solid-state imaging device that can perform accurate imaging even for various applications and light incidence patterns.

Solution to Problem

A solid-state imaging device according to the present invention includes an imaging photodetecting section where M×N pixel units $P_{1,1}$ to $P_{M,N}$ are two-dimensionally arrayed in M rows and N columns, a trigger photodetecting section including a trigger photodiode that generates charge of an amount according to an incident light amount, a trigger data output section that outputs trigger data according to an amount of charge generated in the trigger photodetecting section, and a control section that controls operation of each pixel unit $P_{m,n}$ of the imaging photodetecting section. Here, M and N are each an integer not less than 2, m is an integer not less than 1 and not more than M, and n is an integer not less than 1 and not more than N.

Moreover, each pixel unit $P_{m,n}$ in the device includes a photodiode that generates charge of an amount according to an incident light amount, a first charge accumulating section that accumulates a charge generated in the photodiode, a second charge accumulating section to which a charge accumulated in the first charge accumulating section is transferred, a first initializing section that initializes charge accumulation in the first charge accumulating section, a second initializing section that initializes charge accumulation in the second charge accumulating section, a transfer section that transfers a charge accumulated in the first charge accumulating section to the second charge accumulating section, and an output section that outputs pixel data according to an amount of charge accumulated in the second charge accumulating section to a wiring line $L_n$.

Further, the control section in the device (a) when an absolute value of trigger data output from the trigger data output section has changed into a state of being in excess of a first threshold from a state of being less than the first threshold, and then the state where the absolute value of the trigger data is in excess of the first threshold has continued for a predetermined time $\tau_1$ or more, judges it as a start of a light incidence, and ends an initializing operation by the first initializing section and starts a charge accumulating operation by the first charge accumulating section for the M×N pixel units $P_{1,1}$ to $P_{M,N}$ of the imaging photodetecting section, and (b) when an absolute value of trigger data output from the trigger data output section has changed into a state of being less than a second threshold from a state of being in excess of the second threshold, and then a state where the absolute value of the trigger data is not in excess of the second threshold has continued for a predetermined time $\tau_2$ or more, judges it as an end of a light incidence, and causes a charge transferring operation by the transfer section and a data outputting operation by the output section to be performed for the M×N pixel units $P_{1,1}$ to $P_{M,N}$ of the imaging photodetecting section. Moreover, here, it is preferable that $\tau_2 > \tau_1$.

Advantageous Effects of Invention

The solid-state imaging device according to the present invention can perform accurate imaging even for various applications and light incidence patterns.

DESCRIPTION OF EMBODIMENTS

Hereinafter, embodiments of the present invention will be described in detail with reference to the accompanying drawings. Also, the same components will be denoted with the same reference symbols in the description of the drawings, and overlapping description will be omitted.

Figure 1:
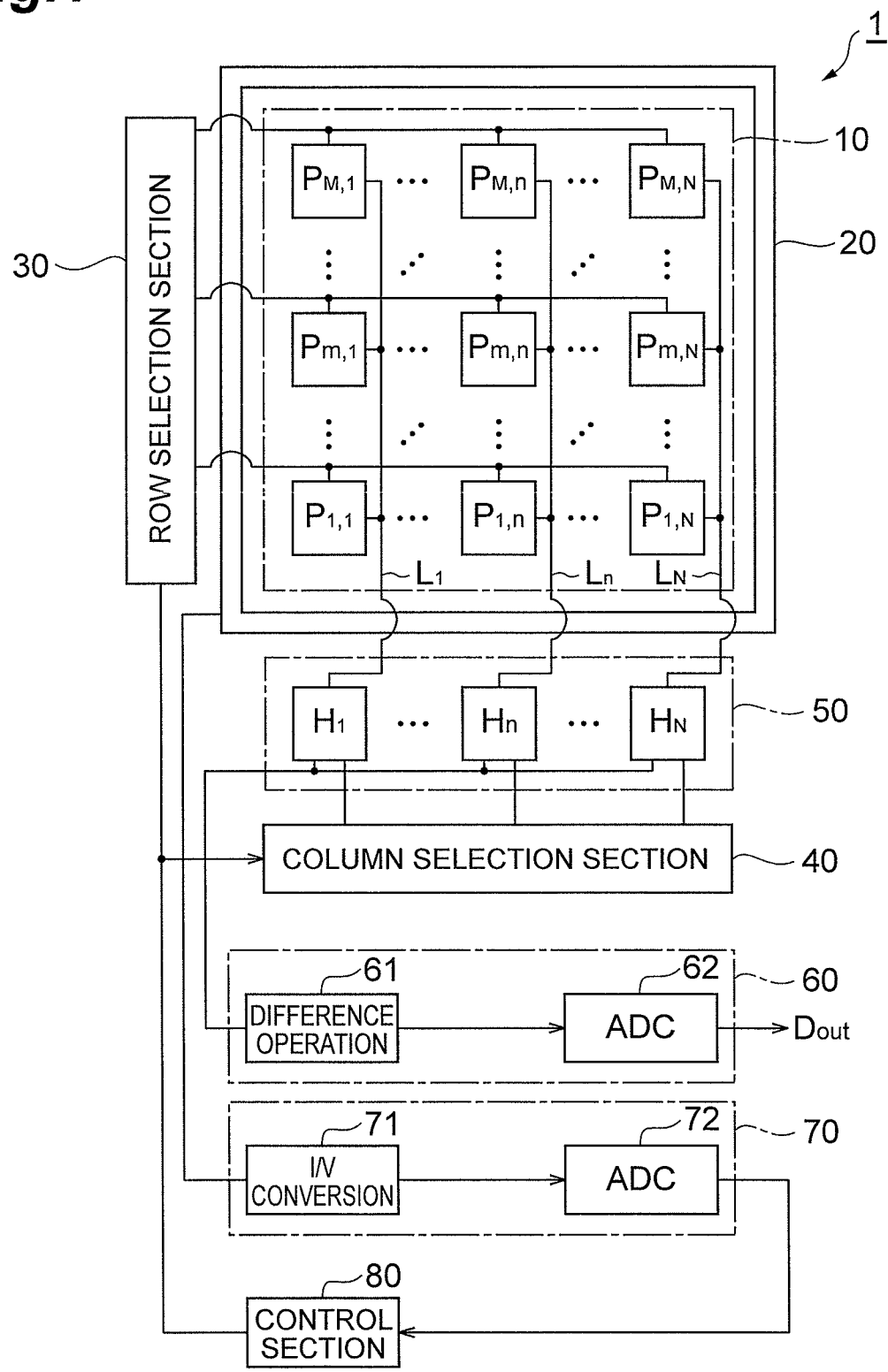
FIG. 1 is a view showing a configuration of a solid-state imaging device 1 according to the present embodiment.

FIG. 1 is a view showing a configuration of a solid-state imaging device 1 according to the present embodiment. The solid-state imaging device 1 shown in this figure includes an imaging photodetecting section 10, a trigger photodetecting section 20, a row selection section 30, a column selection section 40, a holding section 50, a pixel data output section 60, a trigger data output section 70, and a control section 80. In this figure, wiring lines between the elements are omitted or simplified.

Of these elements, at least the imaging photodetecting section 10 and the trigger photodetecting section 20 are formed on a common substrate. Moreover, on this substrate, preferably, the row selection section 30, the column selection section 40, the holding section 50, the pixel data output section 60, and the trigger data output section 70 are also formed. The control section 80 is preferably formed on this substrate, but may be provided separately from this substrate.

The imaging photodetecting section 10 is for taking an image of light made incident thereon, and includes pixel units $P_{1,1}$ to $P_{M,N}$ two-dimensionally arrayed in M rows and N columns. A pixel unit $P_{m,n}$ is located on the m-th row and the n-th column. The M×N pixel units $P_{1,1}$ to $P_{M,N}$ have a common configuration, and include photodiodes that generate charge of amounts according to incident light amounts. Here, M and N are each an integer not less than 2, m is an integer not less than 1 and not more than M, and n is an integer not less than 1 and not more than N.

The trigger photodetecting section 20 is for detecting incidence of light, and includes a trigger photodiode that generates charge of an amount according to an incident light amount. The number and arrangement of trigger photodiodes included in the trigger photodetecting section 20 can be in various modes, but for detecting incidence of light at high sensitivity, it is preferable that a trigger photodiode(s) is provided so as to surround the imaging photodetecting section 10, and it is preferable that the photodetecting area is wide. It is preferable that the trigger photodetecting section 20 includes a single trigger photodiode provided surrounding the imaging photodetecting section 10 as illustrated, and alternatively, it is also preferable that the trigger photodetecting section includes a plurality of trigger photodiodes provided around the imaging photodetecting section 10 and connected in parallel to each other.

In addition, the imaging photodetecting section 10 and the trigger photodetecting section 20 may be covered with a scintillator. In this case, the solid-state imaging device 1 can take an X-ray image as well.

The row selection section 30 instructs each pixel unit $P_{m,n}$ on accumulation of charge generated in the photodiode, and instructs on output of pixel data according to an amount of the charge. The row selection section 30 includes an M-stage shift register circuit, and can designate each row in the imaging photodetecting section 10 by an output bit of each stage of the shift register circuit.

The holding section 50 includes N holding circuits $H_1$ to $H_N$ having a common configuration. A holding circuit $H_n$ is connected to the M pixel units $P_{1,n}$ to $P_{M,n}$ of the n-th column in the imaging photodetecting section 10 by a wiring line $L_n$, is input with pixel data output from any pixel unit $P_{m,n}$ out of these, and holds and outputs the input pixel data. The holding circuit $H_n$ can hold pixel data indicating a signal component superimposed with a noise component as well as hold pixel data indicating a noise component.

The column selection section 40 sequentially designates the N holding circuits $H_1$ to $H_N$ included in the holding section 50 to output pixel data held by the designated n-th holding circuit $H_n$ to the pixel data output section 60. The column selection section 40 includes an N-stage shift register circuit, and can sequentially designate the N holding circuits $H_1$ to $H_N$ by an output bit of each stage of the shift register circuit.

The pixel data output section 60 includes a difference operation circuit 61 and an A/D converter circuit 62. The difference operation circuit 61 is input with pixel data (pixel data indicating a signal component superimposed with a noise component, and pixel data indicating a noise component) output sequentially from the N holding circuits $H_1$ to $H_N$ included in the holding section 50, and outputs pixel data (pixel data indicating a signal component from which a noise component has been removed) according to a difference in the data. The A/D converter circuit 62 is input with the pixel data (analog value) output from the difference operation circuit 61 to apply thereto A/D conversion, and outputs pixel data as a digital value Dout.

The trigger data output section 70 includes an IN converter circuit 71 and an A/D converter circuit 72. The I/V converter circuit 71 is input with a current signal output from the trigger photodetecting section 20, and outputs a voltage value according to this current value. The A/D converter circuit 72 is input with the voltage value (analog value) output from the I/V converter circuit 71 to apply thereto A/D conversion, and outputs trigger data as a digital value.

The control section 80 controls operation of each pixel unit $P_{m,n}$ of the imaging photodetecting section 10 via the row selection section 30. Moreover, the control section 80 also controls operation of each of the column selection section 40 and the pixel data output section 60. The control section 80 judges the start and end of a light incidence based on trigger data output from the trigger data output section 70, and performs control based on the judgment result.

Figure 2:
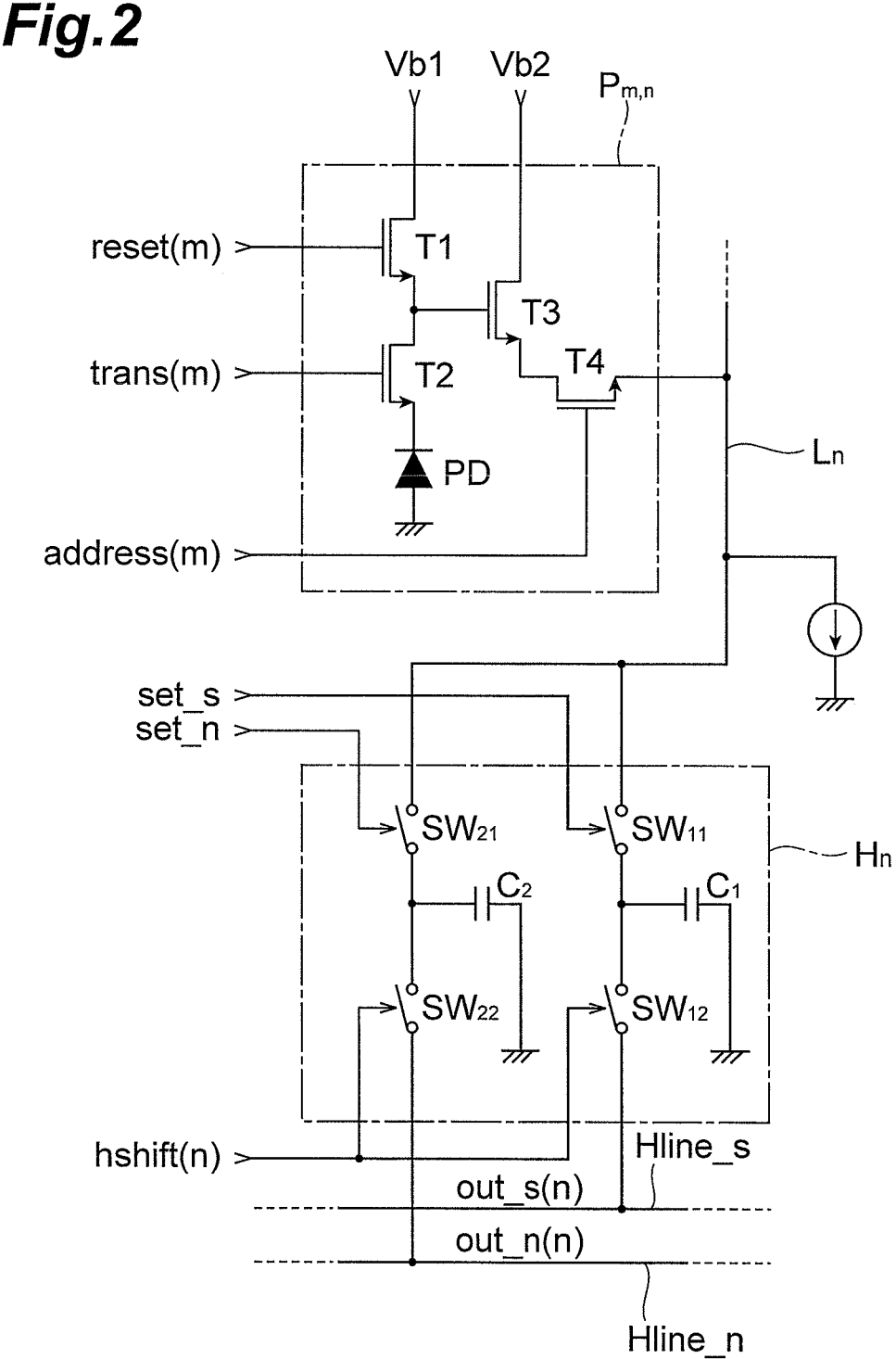
FIG. 2 is a view showing a circuit configuration of each of the pixel unit $P_{m,n}$ and the holding circuit $H_n$ included in the solid-state imaging device 1 according to the present embodiment.

FIG. 2 is a view showing a circuit configuration of each of the pixel unit $P_{m,n}$ and the holding circuit $H_n$ included in the solid-state imaging device 1 according to the present embodiment. In this figure, the pixel unit $P_{m,n}$ is shown as a representative of the M×N pixel units $P_{1,1}$ to $P_{M,N}$, and the holding circuit $H_n$ is shown as a representative of the N holding circuits $H_1$ to $H_N$.

The pixel unit $P_{m,n}$ is of an APS (Active Pixel Sensor) type, and includes a photodiode PD and four transistors T1 to T4. As shown in this figure, the transistor T1, the transistor T2, and the photodiode PD are connected in series in order, a reference voltage Vb1 is input to a drain terminal of the transistor T1, and an anode terminal of the photodiode PD is grounded. The transistor T3 and the transistor T4 are connected in series, a reference voltage Vb2 is input to a drain terminal of the transistor T3, and a source terminal of the transistor T4 is connected to the wiring line $L_n$. A connection point between the transistor T1 and the transistor T2 is connected to a gate terminal of the transistor T3. Moreover, the wiring line $L_n$ is connected with a constant current source.

A reset(m) signal supplied from the row selection section 30 is input to a gate terminal of the transistor T1, a trans(m) signal supplied from the row selection section 30 is input to a gate terminal of the transistor T2, and an address(m) signal supplied from the row selection section 30 is input to a gate terminal of the transistor T4. The reset(m) signal, trans(m) signal, and address(m) signal are commonly input to the N pixel units $P_{m,1}$ to $P_{m,N}$ of the m-th row.

When the reset(m) signal and trans(m) signal are at high level, a junction capacitance section (first charge accumulating section) of the photodiode PD is discharged, and a floating diffusion region (second charge accumulating section) electrically connected to the gate terminal of the transistor T3 is discharged. When the reset(m) signal and trans(m) signal become low level after discharging and further when the address(m) signal becomes high level, a noise component is output from the pixel unit $P_{m,n}$ to the wiring line $L_n$. When the reset(m) signal becomes low level and the trans(m) signal becomes high level, a charge that has been accumulated in the junction capacitance section (first charge accumulating section) of the photodiode PD is transferred to the floating diffusion region (second charge accumulating section) electrically connected to the gate terminal of the transistor T3, and when the address(m) signal becomes high level, a voltage value according to the amount of charge accumulated in the floating diffusion region is output to the wiring line $L_n$ as a signal component.

That is, the transistors T1, T2, as a result of becoming an ON state, act as a first initializing section for initializing charge accumulation in the junction capacitance section (first charge accumulating section) of the photodiode PD. The transistor T1, as a result of becoming an ON state, acts as a second initializing section for initializing charge accumulation in the floating diffusion region (second charge accumulating section). As a result of the transistor T1 becoming an OFF state and the transistor T2 becoming an ON state, these transistors T1, T2 act as a transfer section for transferring a charge that has been accumulated in the junction capacitance section (first charge accumulating section) of the photodiode PD to the floating diffusion region (second charge accumulating section). The transistor T4, as a result of becoming an ON state, acts as an output section for outputting pixel data according to the amount of charge accumulated in the floating diffusion region (second charge accumulating section).

The holding circuit $H_n$ includes two capacitive elements $C_1$, $C_2$ and four switches $SW_{11}$, $SW_{12}$, $SW_{21}$, $SW_{22}$. In this holding circuit $H_n$, the switch $SW_{11}$ and the switch $SW_{12}$ are connected in series and provided between the wiring line $L_n$ and a wiring line Hline_s, one end of the capacitive element $C_1$ is connected to a connection point between the switch $SW_{11}$ and the switch $SW_{12}$, and the other end of the capacitive element $C_1$ is grounded. Moreover, the switch $SW_{21}$ and the switch $SW_{22}$ are connected in series and provided between the wiring line $L_n$ and a wiring line Hline_n, one end of the capacitive element $C_2$ is connected to a connection point between the switch $SW_{21}$ and the switch $SW_{22}$, and the other end of the capacitive element $C_2$ is grounded.

In this holding circuit $H_n$, the switch $SW_{11}$ opens and closes according to the level of a set_s signal supplied from the column selection section 40. The switch $SW_{21}$ opens and closes according to the level of a set_n signal supplied from the column selection section 40. The set_s signal and set_n signal are commonly input to the N holding circuits $H_1$ to $H_N$. The switches $SW_{12}$, $SW_{22}$ open and close according to the level of an hshift(n) signal supplied from the column selection section 40.

In this holding circuit $H_n$, a noise component that has been output from the pixel unit $P_{m,n}$ to the wiring line $L_n$ when the set_n signal switches from high level to low level and the switch $SW_{21}$ opens is held from then on as a voltage value out_n(n) by the capacitive element $C_2$. A signal component that has been output from the pixel unit $P_{m,n}$ to the wiring line $L_n$ when the set_s signal switches from high level to low level and the switch $SW_{11}$ opens is held from then on as a voltage value out_s(n) by the capacitive element $C_1$. Then, when the hshift(n) signal becomes high level, the switch $SW_{12}$ closes, and the voltage value out_s(n) that has been held by the capacitive element $C_1$ is output to the wiring line Hline_s, and the switch $SW_{22}$ closes, and the voltage value out_n(n) that has been held by the capacitive element $C_2$ is output to the wiring line Hline_n. A difference between the voltage value out_s(n) and the voltage value out_n(n) indicates pixel data according to the amount of charge generated in the photodiode PD of the pixel unit $P_{m,n}$.

Figure 3:
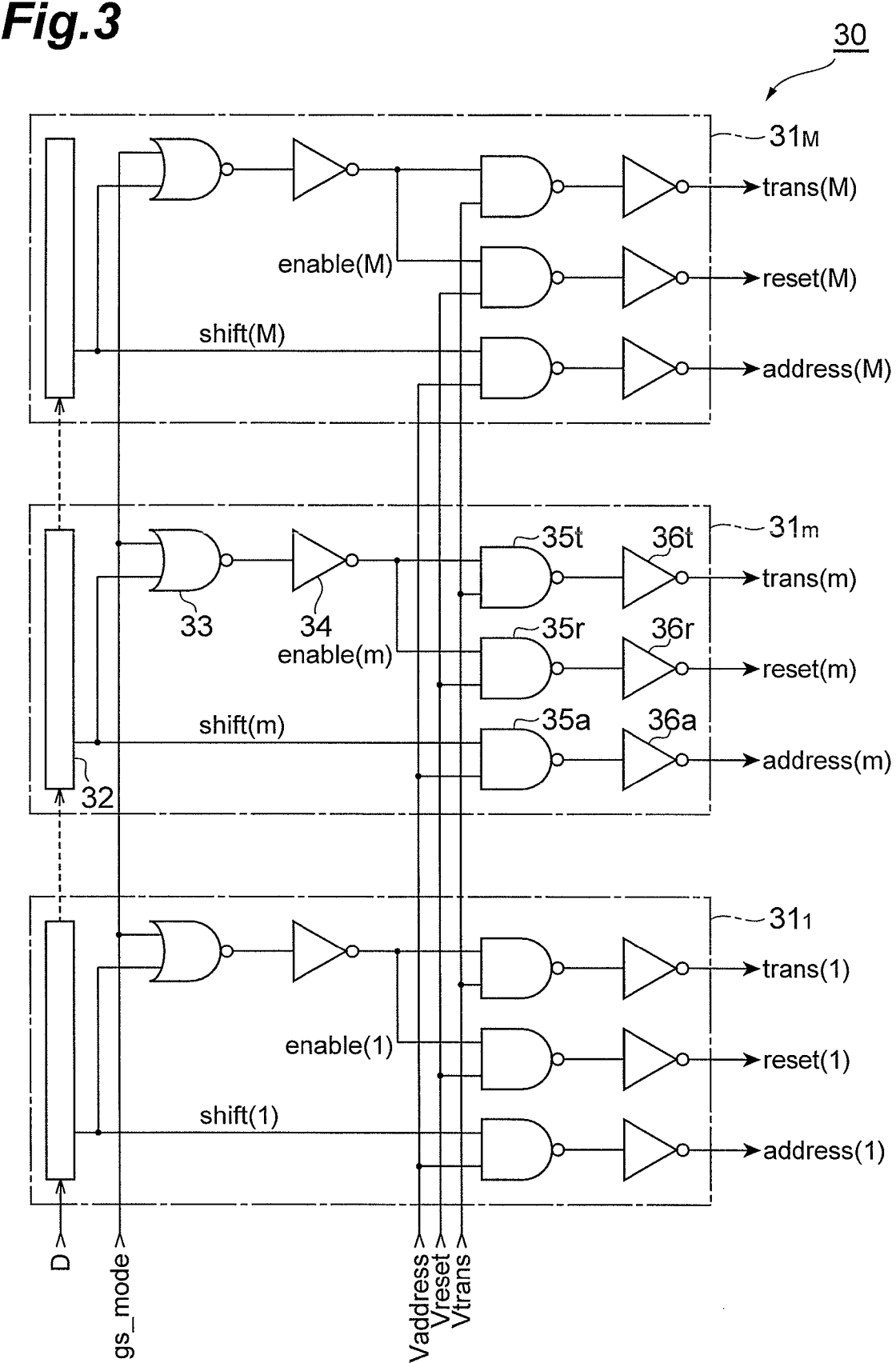
FIG. 3 is a view showing a circuit configuration of a row selection section 30 included in the solid-state imaging device 1 according to the present embodiment.

FIG. 3 is a view showing a circuit configuration of the row selection section 30 included in the solid-state imaging device 1 according to the present embodiment. The row selection section 30 includes M partial circuits $31_1$ to $31_M$ having a common configuration. Each partial circuit $31_m$ includes a latch circuit 32, a NOR circuit 33, an INV circuit 34, a NAND circuit $35_t$, a NAND circuit $35_r$, a NAND circuit $35_a$, an INV circuit $36_t$, an INV circuit $36_r$, and an INV circuit $36_a$.

The respective latch circuits 32 of the M partial circuits $31_1$ to $31_M$ are cascade-connected to compose an M-stage shift register. When a D-signal that becomes high level only for a predetermined period is input to the latch circuit 32 of the first-stage partial circuit $31_1$, from then on, a shift(m) signal to be output from the latch circuit 32 of each partial circuit $31_m$ sequentially becomes high level for a predetermined period.

The NOR circuit 33 of each partial circuit $31_m$ is input with the shift(m) signal output from the latch circuit 32 as well as is input with a gs_mode signal. The INV circuit 34 logically inverts a signal output from the NOR circuit 33, and outputs the logically inverted signal as an enable(m) signal. That is, the NOR circuit 33 and the INV circuit 34 of each partial circuit $31_m$ output the enable(m) signal indicating a logical sum of the shift(m) signal and the gs_mode signal.

The NAND circuit $35_t$ of each partial circuit $31_m$ is input with the enable(m) signal output from the INV circuit 34 as well as is input with a Vtrans signal. The INV circuit $36_t$ logically inverts a signal output from the NAND circuit $35_t$, and outputs the logically inverted signal as a trans(m) signal. That is, the NAND circuit $35_t$ and the INV circuit $36_t$ of each partial circuit $31_m$ output the trans(m) signal indicating a logical product of the enable(m) signal and the Vtrans signal.

The NAND circuit $35_r$ of each partial circuit $31_m$ is input with the enable(m) signal output from the INV circuit 34 as well as is input with a Vreset signal. The INV circuit $36_r$ logically inverts a signal output from the NAND circuit $35_r$, and outputs the logically inverted signal as a reset(m) signal. That is, the NAND circuit $35_r$ and the INV circuit $36_r$ of each partial circuit $31_m$ output the reset(m) signal indicating a logical product of the enable(m) signal and the Vreset signal.

The NAND circuit $35_a$ of each partial circuit $31_m$ is input with the shift(m) signal output from the latch circuit 32 as well as is input with a Vaddress signal. The INV circuit $36_a$ logically inverts a signal output from the NAND circuit $35_a$, and outputs the logically inverted signal as an address(m) signal. That is, the NAND circuit $35_a$ and the INV circuit $36_a$ of each partial circuit $31_m$ output the address(m) signal indicating a logical product of the shift(m) signal and the Vaddress signal.

Each of the gs_mode signal, Vtrans signal, Vreset signal, and Vaddress signal is commonly input to the M partial circuits $31_1$ to $31_M$. Moreover, these signals and the D-signal are supplied from the control section 80 to the row selection section 30. When the gs_mode signal is at high level, the trans(m) signal to be output from each partial circuit $31_m$ is always at the same level as that of the Vtrans signal, and the reset(m) signal to be output from each partial circuit $31_m$ is also always at the same level as that of the Vreset signal.

In contrast thereto, when the gs_mode signal is at low level, in response to the shift(m) signal to be output from the latch circuit 32 of each partial circuit $31_m$ sequentially becoming high level for a predetermined period, the trans(m) signal to be output from each partial circuit $31_m$ sequentially becomes the same level as that of the Vtrans signal for a predetermined period, and the reset(m) signal to be output from each partial circuit $31_m$ also sequentially becomes the same level as that of the Vreset signal for a predetermined period.

Moreover, irrespective of the level of the gs_mode signal, in response to the shift(m) signal to be output from the latch circuit 32 of each partial circuit $31_m$ sequentially becoming high level for a predetermined period, the address(m) signal to be output from each partial circuit $31_m$ sequentially becomes the same level as that of the Vaddress signal for a predetermined period.

Therefore, when the gs_mode signal is at high level, the solid-state imaging device 1 can perform the same simultaneous operation for all pixels as in a global shutter type imaging operation with regard to the trans(m) signal and reset(m) signal to be supplied to each row. In contrast thereto, when the gs_mode signal is at low level, the solid-state imaging device 1 can perform the same row-by-row operation as in a rolling shutter type imaging operation with regard to the trans(m) signal and reset(m) signal to be supplied to each row. Moreover, there is no difference with regard to the address(m) signal.

Figure 4:
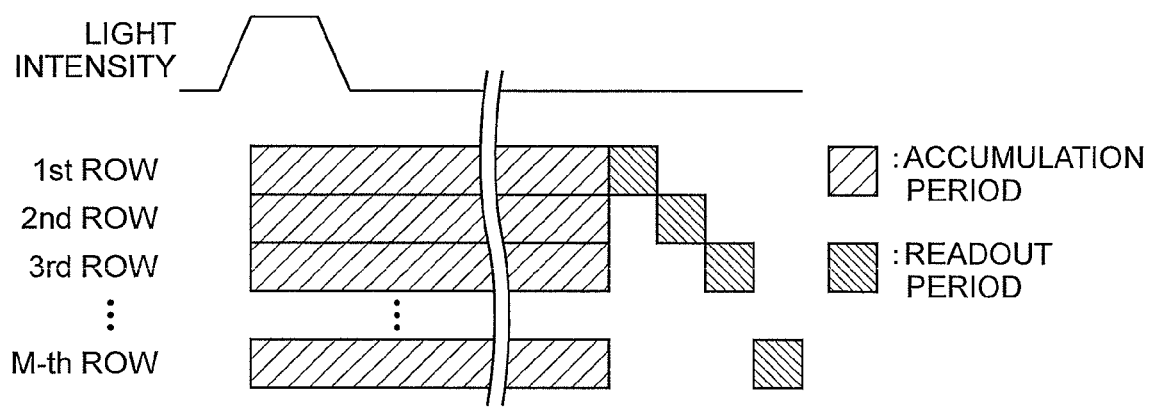
FIG. 4 is a view for explaining a global shutter method.
Figure 5:
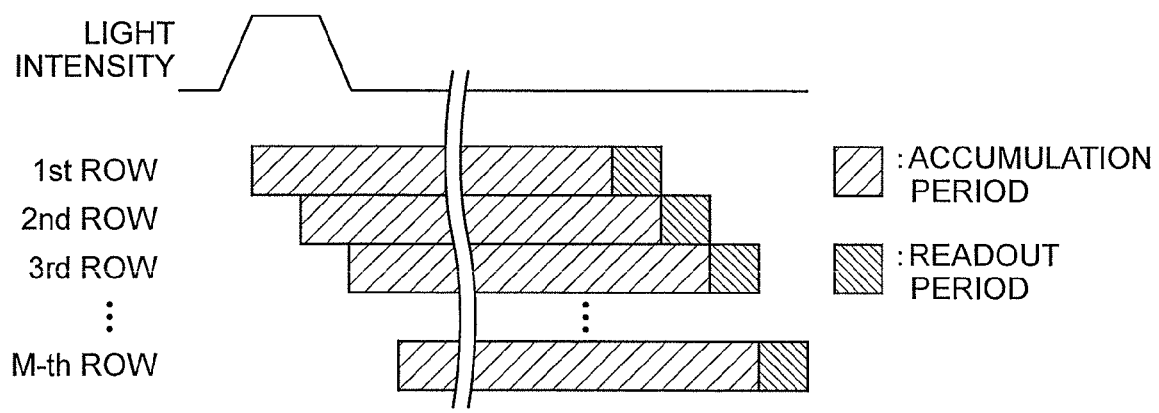
FIG. 5 is a view for explaining a rolling shutter method.
Figure 6:
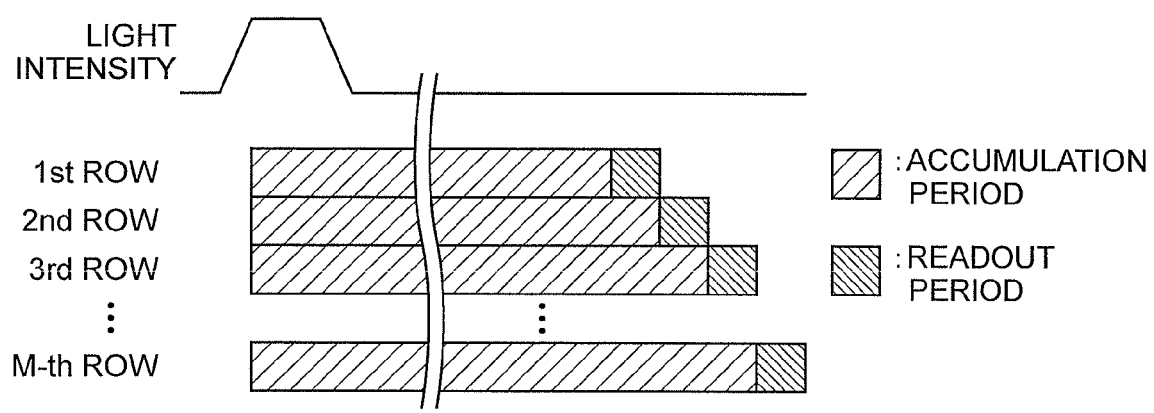
FIG. 6 is a view for explaining a shutter method in the solid-state imaging device 1 according to the present embodiment.

FIG. 4 is a view for explaining a global shutter method. FIG. 5 is a view for explaining a rolling shutter method. Moreover, FIG. 6 is a view for explaining a shutter method in the solid-state imaging device 1 according to the present embodiment. In these figures, the intensity of light that is made incident on the trigger photodetecting section 20 is shown, and the timing of the start of a light incidence that is detected based on trigger data output from the trigger data output section 70 is shown. Moreover, in these figures, the charge accumulation period during which charge is accumulated in the junction capacitance section (first charge accumulating section) of the photodiode PD and the signal readout period during which pixel data according to the amount of charge accumulated in the floating diffusion region (second charge accumulating section) is output from the transistor T4 are shown for each row in the imaging photodetecting section 10.

As shown in FIG. 4, in the global shutter method, the charge accumulation period is common to all rows of the imaging photodetecting section 10, and the signal readout period varies row by row of the imaging photodetecting section 10. In contrast thereto, as shown in FIG. 5, in the rolling shutter method, there is a signal readout period subsequent to a charge accumulation period in each row of the imaging photodetecting section 10, and these periods vary row by row of the imaging photodetecting section 10.

On the other hand, as shown in FIG. 6, in the shutter method of the solid-state imaging device 1 according to the present embodiment, the start of the charge accumulation period is common to all rows of the imaging photodetecting section 10, while the end of the charge accumulation period varies row by row of the imaging photodetecting section 10, and there is a signal readout period subsequent to a charge accumulation period in each row of the imaging photodetecting section 10. The solid-state imaging device 1 according to the present embodiment, by making the gs_mode signal high level, can make the start of the charge accumulation period common to all rows in the imaging photodetecting section 10, and by making the gs_mode signal low level, can perform ending of the charge accumulation period and signal readout sequentially row by row.

In any shutter method, the signal readout periods of the respective rows in the imaging photodetecting section 10 do not overlap each other. Also, in any shutter method, the charge accumulation period of each row of the imaging photodetecting section 10 is started after the timing (arrow in the figure) at which the start of a light incidence is detected based on trigger data output from the trigger data output section 70.

Figure 7:
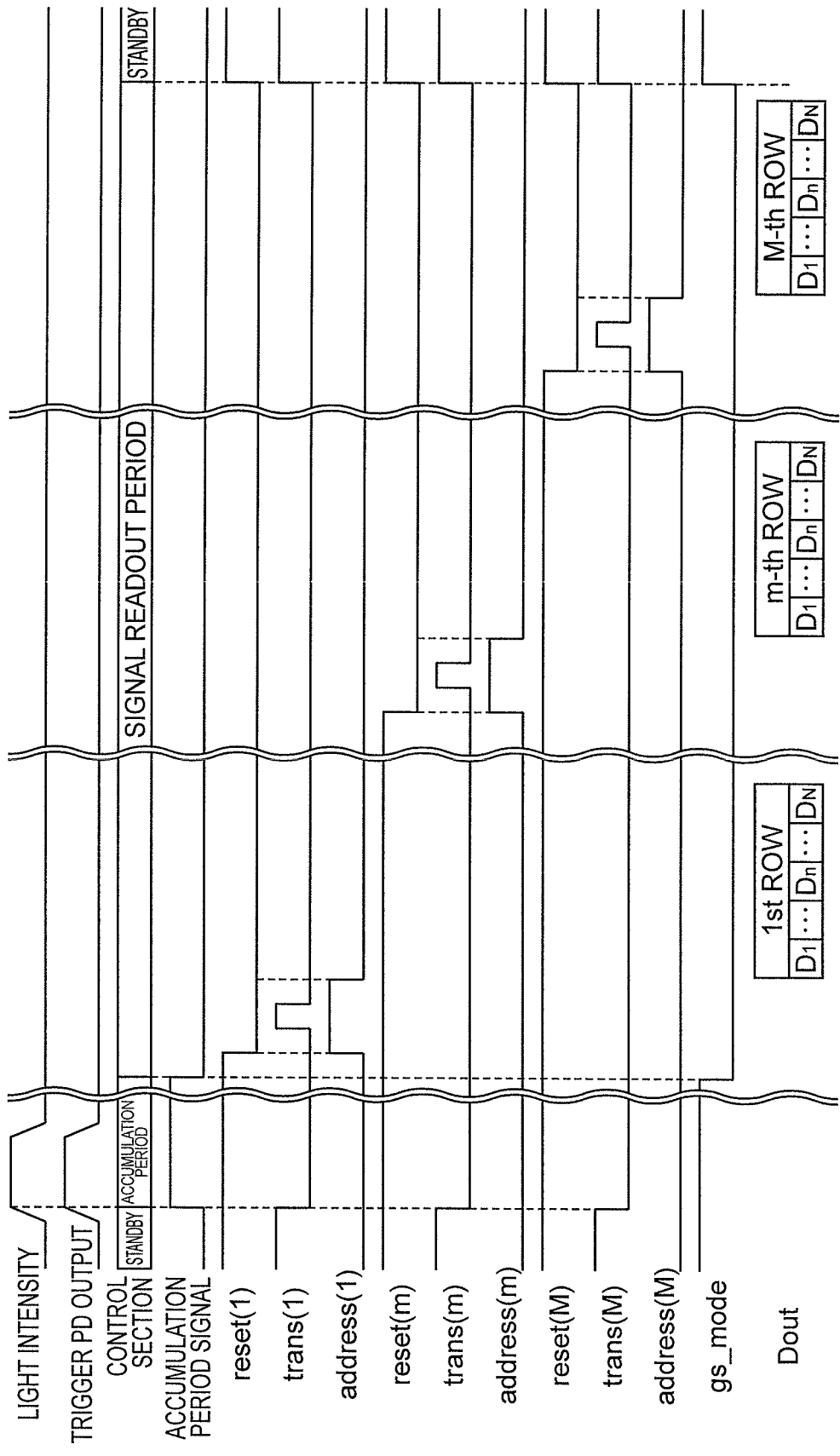
FIG. 7 is a timing chart for explaining operation of the solid-state imaging device 1 according to the present embodiment.

FIG. 7 is a timing chart for explaining operation of the solid-state imaging device 1 according to the present embodiment. This figure shows, in order from the top, the intensity of light incident on the trigger photodetecting section 20, an output current from the trigger photodetecting section 20, control (standby, charge accumulation, signal readout) by the control section 80, a charge accumulation period signal to be supplied to the row selection section 30 from the control section 80, a reset(1) signal, trans(1) signal, and an address(1) signal to be supplied to each pixel unit of the first row, a reset(m) signal, trans(m) signal, and address(m) signal to be supplied to each pixel unit of the m-th row, a reset(M) signal, trans(M) signal, and address(M) signal to be supplied to each pixel unit of the M-th row, a gs_mode signal to be supplied to the row selection section 30, and a digital value Dout to be output from the A/D converter circuit 62.

The control section 80 makes the imaging photodetecting section 10 on standby before a light incidence onto the trigger photodetecting section 20 is started. That is, the control section 80 makes the gs_mode signal high level to make the reset(m) signal and trans(m) signal to be supplied to all pixel units $P_{m,n}$ from the row selection section 30 be high levels equal to those of Vreset and Vtrans, respectively, and make the address(m) signal low level. Accordingly, in all pixel units $P_{m,n}$, the transistors T1, T2 both become an ON state, so that charge accumulation in the junction capacitance section (first charge accumulating section) of the photodiode PD is continuously initialized, and charge accumulation in the floating diffusion region (second charge accumulating section) connected to the gate terminal of the transistor T3 is also continuously initialized.

The control section 80, if judging that a light incidence onto the trigger photodetecting section 20 has been started, brings the imaging photodetecting section 10 into a charge accumulation period. That is, the control section keeps the gs_mode signal high level to keep the reset(m) signal to be supplied to all pixel units $P_{m,n}$ from the row selection section 30 be a high level equal to that of Vreset, change the trans(m) signal to a low level equal to that of Vtrans, and keep the address(m) signal low level. Accordingly, simultaneously in all pixel units $P_{m,n}$, the transistor T2 becomes an OFF state, so that the initializing operation for charge accumulation in the junction capacitance section (first charge accumulating section) of the photodiode PD ends, and the charge accumulating operation by this junction capacitance section (first charge accumulating section) is started. At this time, charge accumulation in the floating diffusion region (second charge accumulating section) connected to the gate terminal of the transistor T3 is continuously initialized.

Then, the control section 80, if judging that a light incidence onto the trigger photodetecting section 20 has been ended, brings the imaging photodetecting section 10 into a signal readout period. That is, the control section 80 causes signal readout to be performed sequentially for each row of the imaging photodetecting section 10 after changing the gs_mode signal to low level. In signal readout from the pixel unit $P_{m,n}$ of the m-th row, the control section changes the reset(m) signal to be supplied to the pixel unit $P_{m,n}$ from the row selection section 30 to low level as well as changes the address(m) signal to high level, then makes the trans(m) signal high level only for a predetermined period, and then returns the address(m) signal to low level. Accordingly, in the pixel unit $P_{m,n}$ of the m-th row, the transistor T1 becomes an OFF state as well as the transistor T4 becomes an ON state, then the transistor T2 becomes an ON state for a predetermined period, and then the transistor T4 returns to an OFF state.

The timing to change the reset(m) signal to low level is immediately before changing the address(m) signal to high level in the example of FIG. 7, but it can be in a period after having changed the trans(m) signal to low level to start accumulation and before changing the address(m) signal to high level. This is because, if it is a state where initialization of charge accumulation in the floating diffusion region has been performed, an increase in noise due to current leakage can be regarded negligible compared to the case where charge is accumulated. Moreover, the timing to change the gs_mode signal to low level may be set to immediately before the reset(1) signal of the first row changes to low level in order to change the reset(m) signal to low level row by row, and may be set to after having changed the reset(m) to low level simultaneously in all pixel units. This is also for the same reason as above.

In the pixel unit $P_{m,n}$ of the m-th row, when the transistors T1, T2 are in an OFF state and the transistor T4 becomes an ON state, the initializing operation for charge accumulation in the floating diffusion region (second charge accumulating section) connected to the gate terminal of the transistor T3 ends, and data (noise component) output to the wiring line $L_n$ from the pixel unit $P_{m,n}$ is held as a voltage value out_n(n) by the capacitive element $C_2$ of the holding circuit $H_n$.

Then, in the pixel unit $P_{m,n}$ of the m-th row, when the transistor T1 is in an OFF state and the transistors T2, T4 become an ON state, a charge that has been accumulated in the junction capacitance section (first charge accumulating section) of the photodiode PD is transferred to the floating diffusion region (second charge accumulating section), and pixel data according to the amount of charge accumulated in the floating diffusion region (second charge accumulating section) is output to the wiring line $L_n$. The data (signal component superimposed with a noise component) output to the wiring line $L_n$ from the pixel unit $P_{m,n}$ at this time is held as a voltage value out_s(n) by the capacitive element $C_1$ of the holding circuit $H_n$.

And, then, sequentially for each holding circuit $H_n$, the voltage value out_s(n) that has been held by the capacitive element $C_1$ is output to the wiring line Hline_s, the voltage value out_n(n) that has been held by the capacitive element $C_2$ is output to the wiring line Hline_n, and data (pixel data indicating a signal component from which a noise component has been removed) according to a difference between the voltage value out_s(n) and the voltage value out_n(n) is obtained by the difference operation circuit 61. Further, the pixel data (analog value) output from the difference operation circuit 61 is AD converted by the A/D converter circuit 62, and a digital value $D_n$ according to the pixel data is output. This digital value $D_n$ indicates the amount of charge generated in the photodiode PD of the pixel unit $P_{m,n}$.

The control section 80 makes the imaging photodetecting section 10 on standby after completing readout up to the last row. That is, the control section 80 makes the gs_mode signal high level to make the reset(m) signal and trans(m) signal to be supplied to all pixel units $P_{m,n}$ from the row selection section 30 high level and make the address(m) signal low level. Accordingly, in all pixel units the transistors T1, T2 both become an ON state, so that charge accumulation in the junction capacitance section (first charge accumulating section) of the photodiode PD is continuously initialized, and charge accumulation in the floating diffusion region (second charge accumulating section) connected to the gate terminal of the transistor T3 is also continuously initialized. Thereafter, the above-described operation is repeated.

As in the above, the solid-state imaging device 1 according to the present embodiment starts a charge accumulating operation simultaneously in all pixel units $P_{m,n}$ at the start of a light incidence, and ends the charge accumulating operation to perform signal readout sequentially for each row after the light incidence ends, and can thus perform correlated double sampling. Moreover, because this solid-state imaging device 1 can perform signal readout immediately after ending the charge accumulating operation, the time until performing signal output after transferring a charge to the floating diffusion region (second charge accumulating section) can be reduced. Therefore, the solid-state imaging device 1 can perform high-accuracy imaging even when the incident period of light to be imaged is considerably short.

Next, a judgment on the start and end of a light incidence by the control section 80 will be described. As the simplest method, the control section 80 can judge, as a light incidence start time, the time where the absolute value of trigger data output from the trigger data output section 70 changed into a state of being in excess of a threshold from a state being less than the threshold, and can judge, as a light incidence end time, the time where the absolute value of trigger data changed into a state of being less than the threshold from a state of being in excess of the threshold.

However, in this simple judging method, an erroneous judgment may be made when trigger data output from the trigger data output section 70 includes noise or when a light incidence is repeated in a pulsed manner over a predetermined period. In particular, when the solid-state imaging device 1 is used for intraoral X-ray imaging, it is highly likely that such an erroneous judgment is made.

For example, a solid-state imaging device to be used for intraoral X-ray imaging is a portable device and thus impacts such as falls may occur in some cases, and a patient may bite the device body or its cable in some other cases, so that noise may be momentarily superimposed on trigger data due to these factors.

Figure 8:
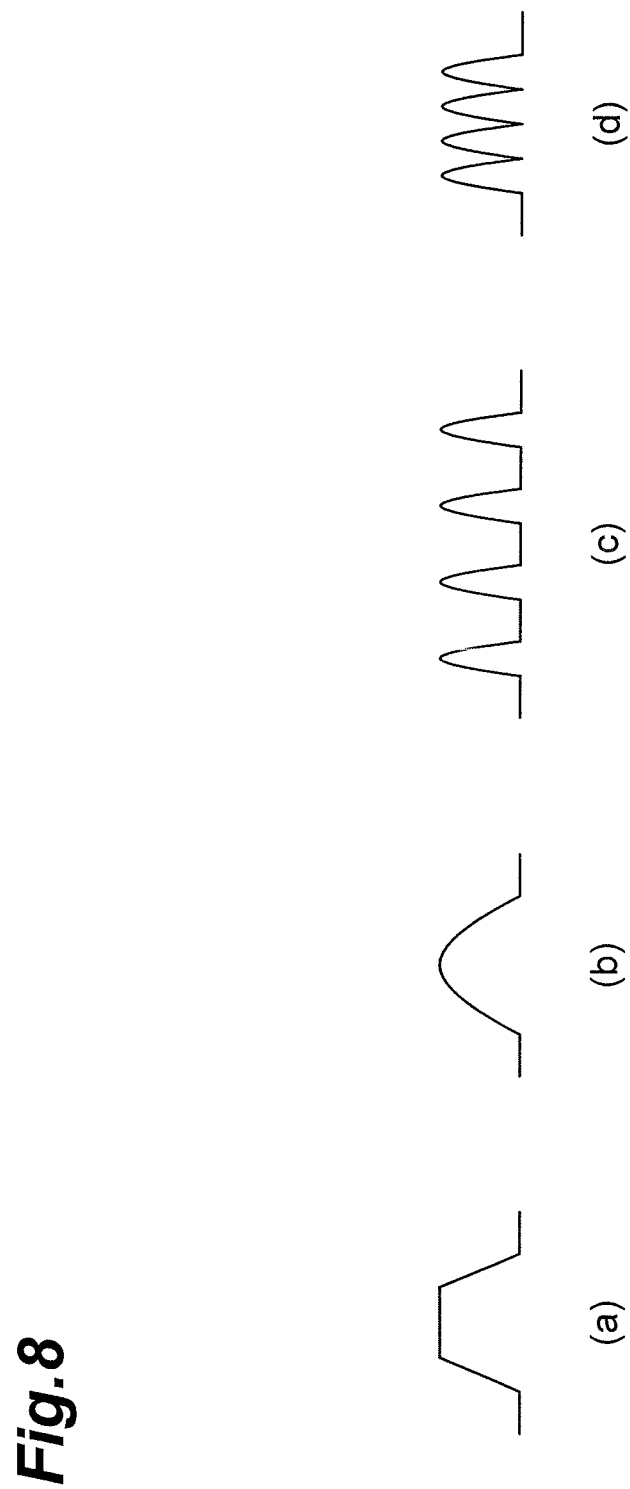
FIG. 8 is a view showing examples of light incidence patterns.

Moreover, for the solid-state imaging device to be used for intraoral X-ray imaging, a single X-ray pulse may be made incident in some cases, and a plurality of X-ray pulses may be repeatedly made incident over a predetermined period in some other cases. FIG. 8 is a view showing examples of light incidence patterns. There is only an incidence of a single pulse in the light incidence patterns shown in (a) and (b) in FIG. 8, while an incidence of a plurality of light pulses is repeated over a predetermined period in the light incidence patterns shown in (c) and (d) in FIG. 8. In (c) in FIG. 8, an incidence interval exists between one light pulse and the next light pulse. In (d) in FIG. 8, one light pulse is followed immediately by an incidence of the next light pulse.

In the case of the light incidence patterns shown in (c) and (d) in FIG. 8, if charge accumulation is ended in each pixel unit $P_{m,n}$ as a result of judging, as a light incidence end time, the time where the absolute value of trigger data changed into a state of being less than a threshold from a state of being in excess of the threshold, the second light pulse onward out of the plurality of light pulses cannot be imaged.

The judging method by the control section 80 to be described in the following allows accurately judging the start and end of a light incidence even when trigger data output from the trigger data output section 70 includes noise or when a light incidence is repeated in a pulsed manner over a predetermined period.

Figure 9:
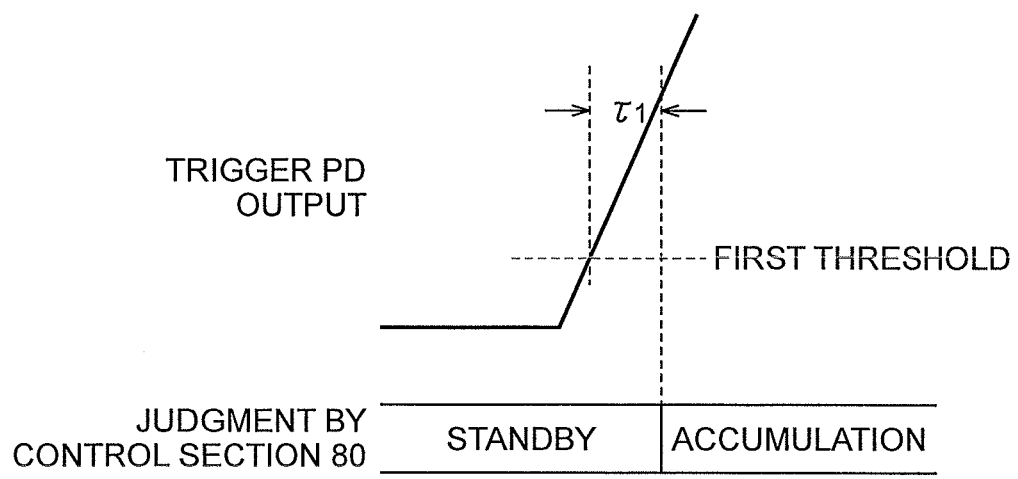
FIG. 9 is a view for explaining a judgment on a light incidence start by a control section 80 included in the solid-state imaging device 1 according to the present embodiment.
Figure 10:
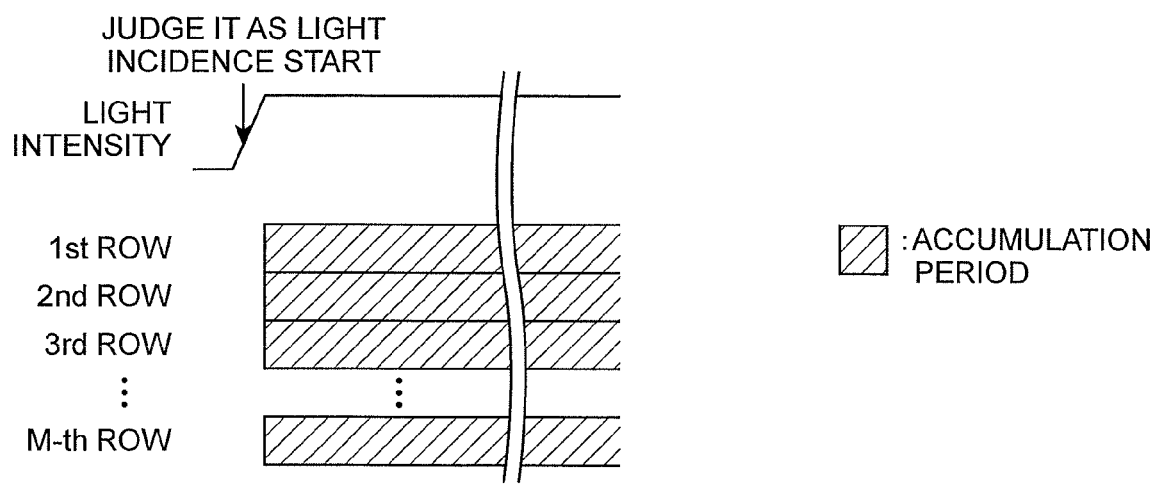
FIG. 10 is a view showing a relationship between a judgment on a light incidence start and a charge accumulating operation start in the solid-state imaging device 1 according to the present embodiment.

FIG. 9 is a view for explaining a judgment on a light incidence start by the control section 80 included in the solid-state imaging device 1 according to the present embodiment. As shown in FIG. 9, when the absolute value of trigger data output from the trigger data output section 70 has changed into a state of being in excess of a first threshold from a state of being less than the first threshold and then the state where the absolute value of trigger data is in excess of the first threshold has continued for a predetermined time $\tau_1$ or more, the control section 80 judges it as a light incidence start. Further, the control section 80, as shown in FIG. 10, if judging it as a light incidence start, causes a change from a standby state into a charge accumulating operation simultaneously for each pixel unit $P_{m,n}$ of the imaging photodetecting section 10.

On the other hand, even when the absolute value of trigger data has changed into a state of being in excess of a first threshold from a state of being less than the first threshold, if the subsequent duration of the state where the absolute value of trigger data is in excess of the first threshold is less than the predetermined time $\tau_1$, the control section 80 judges that the trigger data is superimposed with noise, and does not judge it as a light incidence start. At this time, the control section 80 makes each pixel unit $P_{m,n}$ of the imaging photodetecting section 10 remain on standby, and continuously initializes the junction capacitance section of the photodiode PD of each pixel unit $P_{m,n}$.

Here, the time $\tau_1$ is set to a value larger than the pulse width of noise to be superimposed on trigger data to be output from the trigger data output section 70, and is set to, for example, 100 μs or more.

Figure 11:
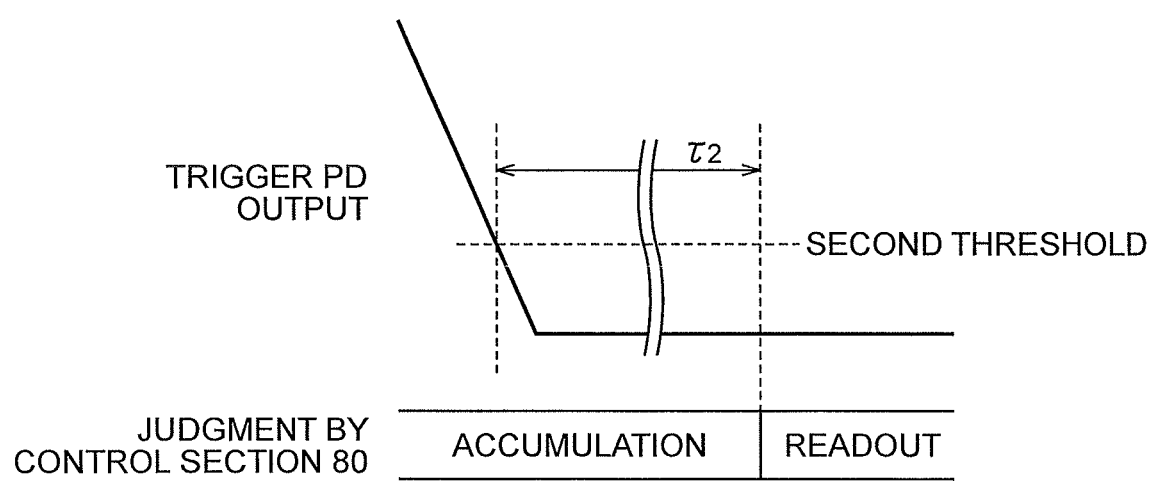
FIG. 11 is a view for explaining a judgment on a light incidence end by the control section 80 included in the solid-state imaging device 1 according to the present embodiment.
Figure 12:
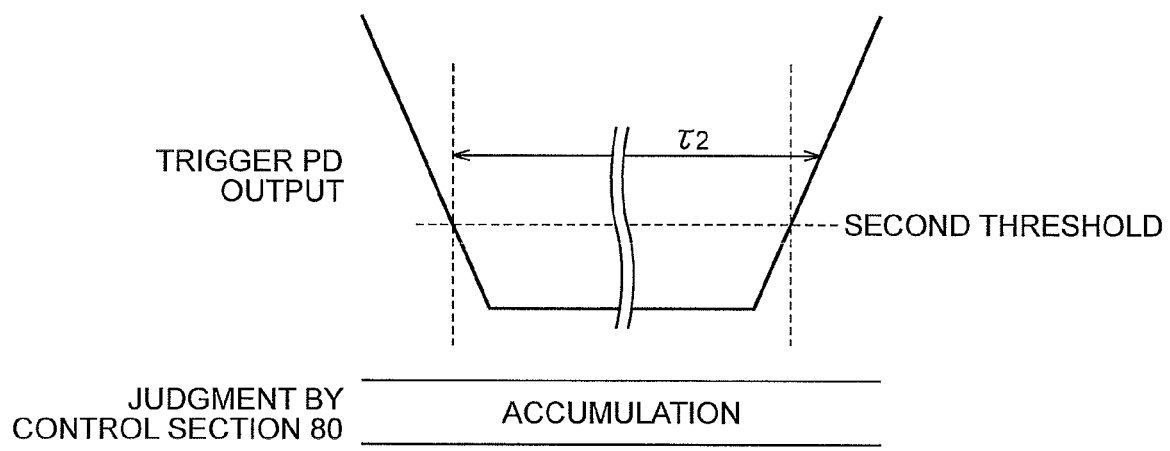
FIG. 12 is a view for explaining a judgment on a light incidence end by the control section 80 included in the solid-state imaging device 1 according to the present embodiment.
Figure 13:
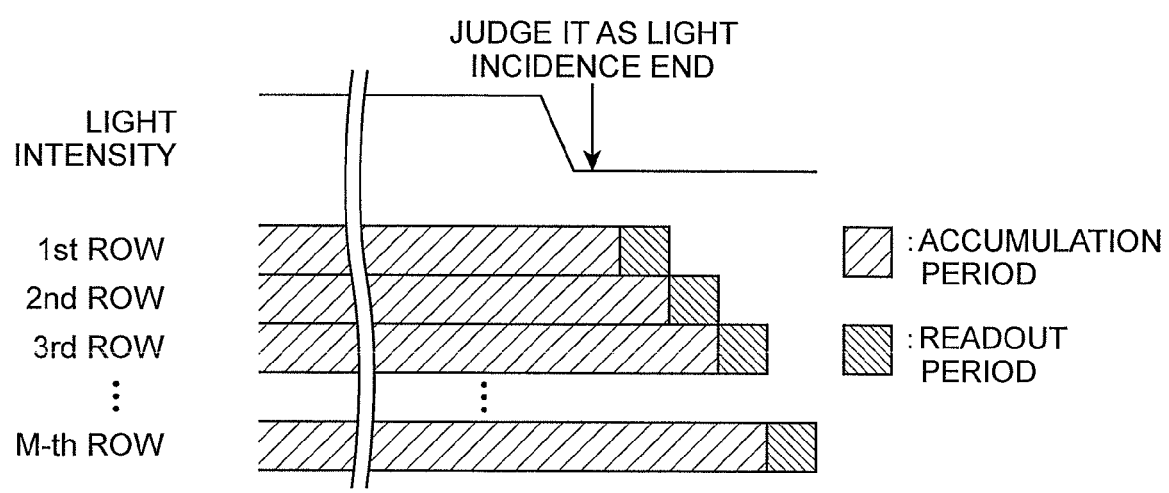
FIG. 13 is a view showing a relationship between a judgment on a light incidence end and a charge accumulating operation end and signal readout in the solid-state imaging device 1 according to the present embodiment.
Figure 14:
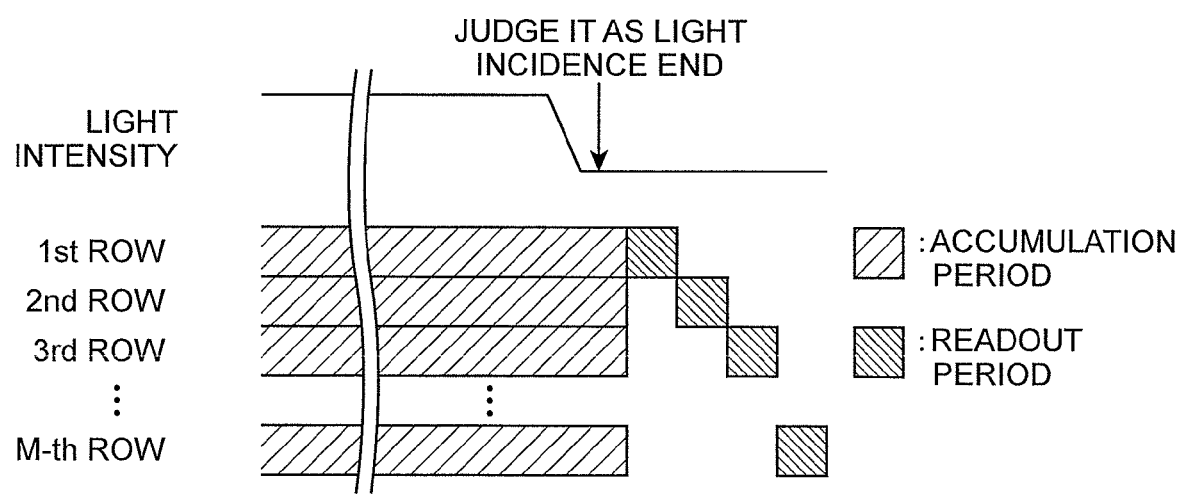
FIG. 14 is a view showing a relationship between a judgment on a light incidence end and a charge accumulating operation end and signal readout in the solid-state imaging device 1 according to the present embodiment.

FIG. 11 and FIG. 12 are views for explaining a judgment on a light incidence end by the control section 80 included in the solid-state imaging device 1 according to the present embodiment. As shown in these figures, when the absolute value of trigger data output from the trigger data output section 70 has changed into a state of being less than a second threshold from a state of being in excess of the second threshold, and then a state where the absolute value of trigger data is not in excess of the second threshold has continued for a time $\tau_2$ or more, the control section 80 judges it as a light incidence end. Further, the control section 80, as shown in FIG. 13, if judging it as a light incidence end, ends the charge accumulating operation to cause the signal readout operation to be performed sequentially for each row of the imaging photodetecting section 10. Alternatively, the control section 80, as shown in FIG. 14, if judging it as a light incidence end, may end the charge accumulating operation simultaneously for each row of the imaging photodetecting section 10, and then cause the signal readout operation to be performed sequentially row by row.

On the other hand, even when the absolute value of trigger data has changed into a state of being less than a second threshold from a state of being in excess of the second threshold, when the absolute value of trigger data exceeds the second threshold in the following time $\tau_2$, the control section 80 judges that the light incidence has not yet ended. At this time, the control section 80 makes each pixel unit $P_{m,n}$ of the imaging photodetecting section 10 continue the charge accumulating operation.

Figure 15:
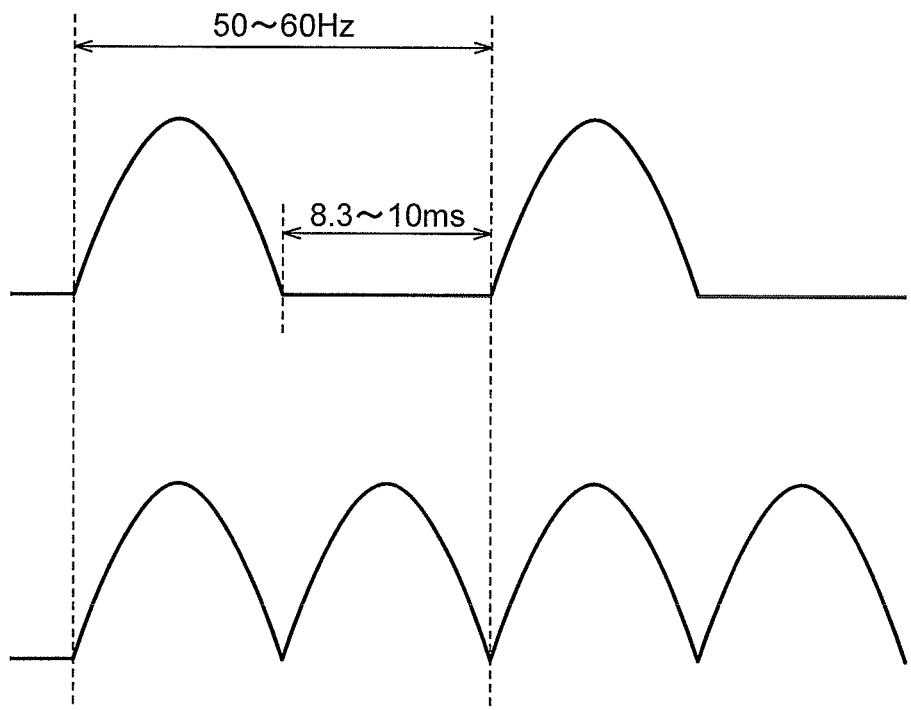
FIG. 15 is a view showing examples of light incidence patterns.

Moreover, the time $\tau_2$ is appropriately set according to the repetition period of light incident pulses. For example, when a light source (X-ray source) is driven by a commercial power supply having a frequency of 50 Hz or 60 Hz, the patterns of light pulses emitted from the light source and made incident on the solid-state imaging device 1 are as shown in FIG. 15. The repetition frequency of light pulses is 50 Hz or 60 Hz as shown in (a) in FIG. 15, or a double frequency thereof as shown in (b) in FIG. 15. As shown in (a) in FIG. 15, since the time interval from a non-incidence to incidence of light is 10 ms at the maximum, it is preferable that the time $\tau_2$ is set 12.5 ms or more.

Figure 16:
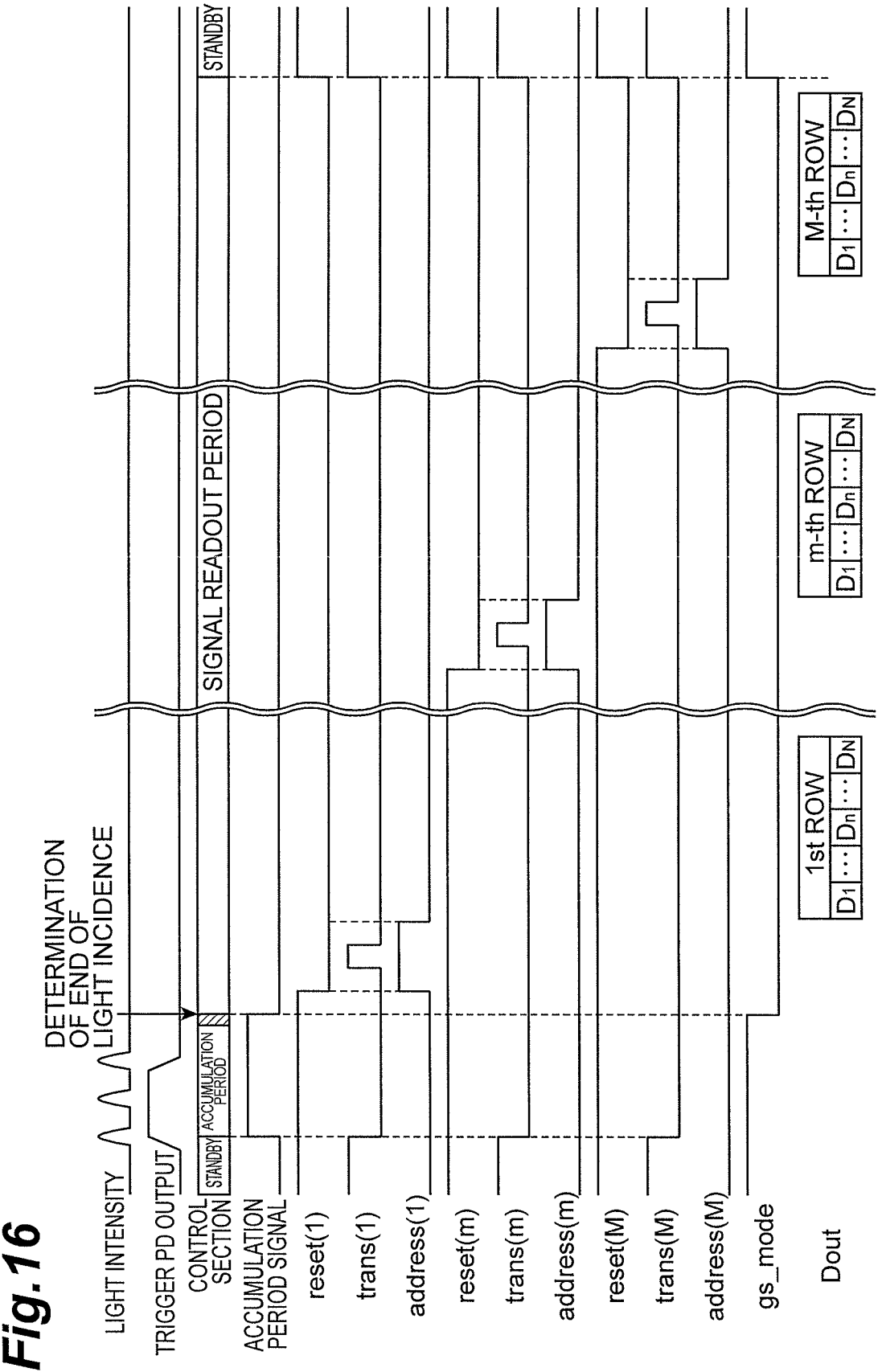
FIG. 16 is a timing chart for explaining operation of the solid-state imaging device 1 according to the present embodiment.

FIG. 16 is a timing chart for explaining operation of the solid-state imaging device 1 according to the present embodiment. FIG. 16 is a timing chart in the case of the light incidence patterns shown in (c) and (d) in FIG. 8 ((a) and (b) in FIG. 15). In this case, the control section 80 judges it as a light incidence end after the end of an incidence of the last light pulse out of the plurality of light pulses to bring the imaging photodetecting section 10 into a signal readout period. The other operations are the same as those described with FIG. 7.

The solid-state imaging device according to the present invention is not limited to the embodiment and configuration example described above, and various modifications can be made.

In the solid-state imaging device according to the above-described embodiment, used is a configuration including an imaging photodetecting section where M×N pixel units $P_{1,1}$ to $P_{M,N}$ are two-dimensionally arrayed in M rows and N columns, a trigger photodetecting section including a trigger photodiode that generates charge of an amount according to an incident light amount, a trigger data output section that outputs trigger data according to an amount of charge generated in the trigger photodetecting section, and a control section that controls operation of each pixel unit $P_{m,n}$ of the imaging photodetecting section. Here, M and N are each an integer not less than 2, m is an integer not less than 1 and not more than M, and n is an integer not less than 1 and not more than N.

Moreover, each pixel unit $P_{m,n}$ includes a photodiode that generates charge of an amount according to an incident light amount, a first charge accumulating section that accumulates a charge generated in the photodiode, a second charge accumulating section to which a charge accumulated in the first charge accumulating section is transferred, a first initializing section that initializes charge accumulation in the first charge accumulating section, a second initializing section that initializes charge accumulation in the second charge accumulating section, a transfer section that transfers a charge accumulated in the first charge accumulating section to the second charge accumulating section, and an output section that outputs pixel data according to an amount of charge accumulated in the second charge accumulating section to a wiring line $L_n$.

Further, the control section (a) when an absolute value of trigger data output from the trigger data output section has changed into a state of being in excess of a first threshold from a state of being less than the first threshold, and then the state where the absolute value of the trigger data is in excess of the first threshold has continued for a predetermined time or more, judges it as a start of a light incidence, and ends an initializing operation by the first initializing section and starts a charge accumulating operation by the first charge accumulating section for the M×N pixel units $P_{1,1}$ to $P_{M,N}$ of the imaging photodetecting section, and (b) when an absolute value of trigger data output from the trigger data output section has changed into a state of being less than a second threshold from a state of being in excess of the second threshold, and then a state where the absolute value of the trigger data is not in excess of the second threshold has continued for a time $\tau_2$ or more, judges it as an end of a light incidence, ends an initializing operation by the second initializing section, and causes a charge transferring operation by the transfer section and a data outputting operation by the output section to be performed for the M×N pixel units $P_{1,1}$ to $P_{M,N}$ of the imaging photodetecting section. Moreover, it is preferable that $\tau_2 > \tau_1$.

It is preferable that the solid-state imaging device having the above-described configuration further includes a holding section including N holding circuits $H_1$ to $H_N$ that are input with and hold pixel data output from the pixel unit $P_{m,n}$ of the imaging photodetecting section, and a pixel data output section that is input with pixel data held and output by each holding circuit $H_n$ and outputs the pixel data after applying operation. In this case, each holding circuit $H_n$ is connected with M pixel units $P_{1,n}$ to $P_{M,n}$ of the n-th column and by a wiring line $L_n$ in the imaging photodetecting section, is input with and holds pixel data indicating a noise component output to the wiring line $L_n$ from the pixel unit $P_{m,n}$ as well as is input with and holds pixel data indicating a signal component superimposed with a noise component output to the wiring line $L_n$ from the pixel unit $P_{m,n}$, and outputs these two holding pixel data. Moreover, the pixel data output section is input with two pixel data held and output by each holding circuit $H_n$, and outputs pixel data according to a difference between these two pixel data.

Moreover, it is preferable that the predetermined time $\tau_2$ is ten times or more longer than that the predetermined time $\tau_1$.

INDUSTRIAL APPLICABILITY

The present invention can be used as a solid-state imaging device capable of performing accurate imaging even for various applications and light incidence patterns.

REFERENCE SIGNS LIST

1—solid-state imaging device, 10—imaging photodetecting section, 20—trigger photodetecting section, 30—row selection section, 40—column selection section, 50—holding section, 60—pixel data output section, 61—difference operation circuit, 62—A/D converter circuit, 70—trigger data output section, 71—I/V converter circuit, 72—A/D converter circuit, 80—control section, $P_{1,1}$ to $P_{M,N}$—pixel unit.

The invention claimed is:
1. A solid-state imaging device comprising an imaging photodetecting section where M×N pixel units $P_{1,1}$ to $P_{M,N}$ are two-dimensionally arrayed in M rows and N columns, a trigger photodetecting section including a trigger photodiode that generates charge of an amount according to an incident light amount, a trigger data output section that outputs trigger data according to an amount of charge generated in the trigger photodetecting section, and a control section that controls operation of each pixel unit $P_{m,n}$ of the imaging photodetecting section, wherein each pixel unit $P_{m,n}$ includes a photodiode that generates charge of an amount according to an incident light amount, a first charge accumulating section that accumulates a charge generated in the photodiode, a second charge accumulating section to which a charge accumulated in the first charge accumulating section is transferred, a first initializing section that initializes charge accumulation in the first charge accumulating section, a second initializing section that initializes charge accumulation in the second charge accumulating section, a transfer section that transfers a charge accumulated in the first charge accumulating section to the second charge accumulating section, and an output section that outputs pixel data according to an amount of charge accumulated in the second charge accumulating section to a wiring line $L_n$, and the control section, when an absolute value of trigger data output from the trigger data output section has changed into a state of being in excess of a first threshold from a state of being less than the first threshold, and then the state where the absolute value of the trigger data is in excess of the first threshold has continued for a predetermined time $\tau_1$ or more, judges it as a start of a light incidence, and ends an initializing operation by the first initializing section and starts a charge accumulating operation by the first charge accumulating section for the M×N pixel units $P_{1,1}$ to $P_{M,N}$ of the imaging photodetecting section, and when an absolute value of trigger data output from the trigger data output section has changed into a state of being less than a second threshold from a state of being in excess of the second threshold, and then a state where the absolute value of the trigger data is not in excess of the second threshold has continued for a predetermined time $\tau_2$ or more, judges it as an end of a light incidence, and causes a charge transferring operation by the transfer section and a data outputting operation by the output section to be performed for the M×N pixel units $P_{1,1}$ to $P_{M,N}$ of the imaging photodetecting section (provided that M and N are each an integer not less than 2, m is an integer not less than 1 and not more than M, n is an integer not less than 1 and not more than N, and $\tau_2 > \tau_1$).

2. The solid-state imaging device according to claim 1, further comprising a holding section including N holding circuits $H_1$ to $H_N$ that are input with and hold pixel data output from the pixel unit $P_{m,n}$ of the imaging photodetecting section, and a pixel data output section that is input with pixel data held and output by each holding circuit $H_n$ and outputs the pixel data after applying operation, wherein each holding circuit $H_n$ is connected with M pixel units $P_{1,n}$ to $P_{M,n}$ of the n-th column and by the wiring line $L_n$ in the imaging photodetecting section, is input with and holds pixel data indicating a noise component output to the wiring line $L_n$ from the pixel unit $P_{m,n}$ as well as is input with and holds pixel data indicating a signal component superimposed with a noise component output to the wiring line $L_n$ from the pixel unit $P_{m,n}$, and outputs these two holding pixel data, and the pixel data output section is input with two pixel data held and output by each holding circuit $H_n$, and outputs pixel data according to a difference between these two pixel data.

3. The solid-state imaging device according to claim 1, wherein the predetermined time $\tau_2$ is ten times or more longer than the predetermined time $\tau_1$.

* * * * *